United States Patent
Brueckner et al.

(10) Patent No.: US 12,343,113 B2
(45) Date of Patent: Jul. 1, 2025

(54) HYBRID OPTICAL SYSTEM

(71) Applicant: ATONARP INC., Tokyo (JP)

(72) Inventors: Lukas Brueckner, Tokyo (JP); David Anderson, Fremont, CA (US); Prakash Sreedhar Murthy, Tokyo (JP)

(73) Assignee: ATONARP INC., Tokyo (JP)

( * ) Notice: Subject to any disclaimer, the term of this patent is extended or adjusted under 35 U.S.C. 154(b) by 0 days.

(21) Appl. No.: 18/588,108

(22) Filed: Feb. 27, 2024

(65) Prior Publication Data

US 2024/0197182 A1 Jun. 20, 2024

Related U.S. Application Data

(63) Continuation of application No. 17/420,152, filed as application No. PCT/JP2020/017447 on Apr. 23, 2020, now Pat. No. 11,944,407.

(Continued)

(51) Int. Cl.
 *G01N 21/65* (2006.01)
 *A61B 5/00* (2006.01)
 (Continued)

(52) U.S. Cl.
 CPC .............. *A61B 5/0066* (2013.01); *G01J 3/44* (2013.01); *G01N 21/4795* (2013.01); *G01N 21/65* (2013.01); *G01N 2021/653* (2013.01)

(58) Field of Classification Search
 CPC A61B 5/0066; A61B 5/0075; G01N 21/4795; G01N 21/65; G01N 2021/653; G01J 3/44
 See application file for complete search history.

(56) References Cited

U.S. PATENT DOCUMENTS 10,337,995 B2 7/2019 Yi
11,083,375 B2 8/2021 Boppart et al.
(Continued)

FOREIGN PATENT DOCUMENTS

EP 2211219 A2 7/2010
JP 2009222531 A 10/2009
(Continued)

OTHER PUBLICATIONS

Zheltikov, A.M. (2000), Coherent anti-Stokes Raman scattering: from proof-of-the-principle experiments to femtosecond CARS and higher order wave-mixing generalizations. J. Raman Spectrosc., 31: 653-667. https://doi.org/10.1002/1097-4555(200008/09)31:8/9<653::AID-JRS597>3.0.CO;2-W (Year: 2000).*

(Continued)

*Primary Examiner* — Kara E. Geisel
*Assistant Examiner* — Jonathon Cook
(74) *Attorney, Agent, or Firm* — Buchanan Ingersoll & Rooney PC

(57) ABSTRACT

An optical system includes a first optical path configured to supply a first light with a first range of wavelengths; a second optical path configured to supply a second light with a second range of wavelengths shorter than the first range of wavelengths; a third optical path configured to supply a third light with a third range of wavelengths shorter than the second range of wavelengths; an optical I/O unit configured to emit the first light, the second light and the third light to a target and acquire a light from the target; a reference unit configured to split off a reference light from the third light; and a detector that includes a range of detection wavelengths shared with a CARS light and an interference light.

12 Claims, 11 Drawing Sheets

Related U.S. Application Data

(60) Provisional application No. 62/840,001, filed on Apr. 29, 2019.

(51) Int. Cl.
   *G01J 3/44* (2006.01)
   *G01N 21/47* (2006.01)

(56) References Cited

U.S. PATENT DOCUMENTS

| | | | |
|---|---|---|---|
| 2008/0309931 | A1 | 12/2008 | Silberberg et al. |
| 2010/0188496 | A1* | 7/2010 | Xie .................. G01N 21/65 348/79 |
| 2012/0050720 | A1* | 3/2012 | Kim ..................... G01J 3/10 356/51 |
| 2012/0188538 | A1 | 7/2012 | Patil et al. |
| 2014/0253919 | A1 | 9/2014 | Yui |
| 2014/0268131 | A1* | 9/2014 | Tamada ............. G01J 3/0218 356/301 |
| 2016/0076940 | A1 | 3/2016 | Kimura |
| 2016/0238532 | A1* | 8/2016 | Freudiger .............. G02B 21/16 |
| 2017/0023482 | A1* | 1/2017 | Cicerone ............. G02B 21/365 |
| 2019/0137402 | A1 | 5/2019 | Toida |
| 2019/0302437 | A1 | 10/2019 | Hillman |
| 2022/0087530 | A1 | 3/2022 | Brueckner et al. |

FOREIGN PATENT DOCUMENTS

| | | |
|---|---|---|
| JP | 2009258071 A | 11/2009 |
| JP | 2010002256 A | 1/2010 |
| JP | 2018009871 A | 1/2018 |
| WO | 2010106376 A1 | 9/2010 |
| WO | 2014061147 A1 | 4/2014 |
| WO | 2014180986 A1 | 11/2014 |
| WO | 2014189379 A1 | 11/2014 |

OTHER PUBLICATIONS

W. M. Tolles, J. W. Nibler, J. R. McDonald, and A. B. Harvey, "A Review of the Theory and Application of Coherent Anti-Stokes Raman Spectroscopy (CARS)," Appl. Spectrosc. 31, 253-271 (1977) (Year: 1977).*

R. F. Begley, A. B. Harvey, R. L. Byer; Coherent anti-Stokes Raman spectroscopy. Appl. Phys. Lett. Oct. 1, 1974; 25 (7): 387-390. https://doi.org/10.1063/1.1655519 (Year: 1974).*

International Search Report (PCT/ISA/210) and Written Opinion (PCT/ISA/237) mailed on Aug. 18, 2020, by the Japanese Patent Office as the International Searching Authority for International Application No. PCT/JP2020/017447. (7 pages).

Yuri Paskover et al., "Single-shot two dimensional time resolved coherent anti Stokes Raman Scattering," Opt. Express 15, pp. 1700-1705 (Year: 2007).

* cited by examiner

[Fig. 1]
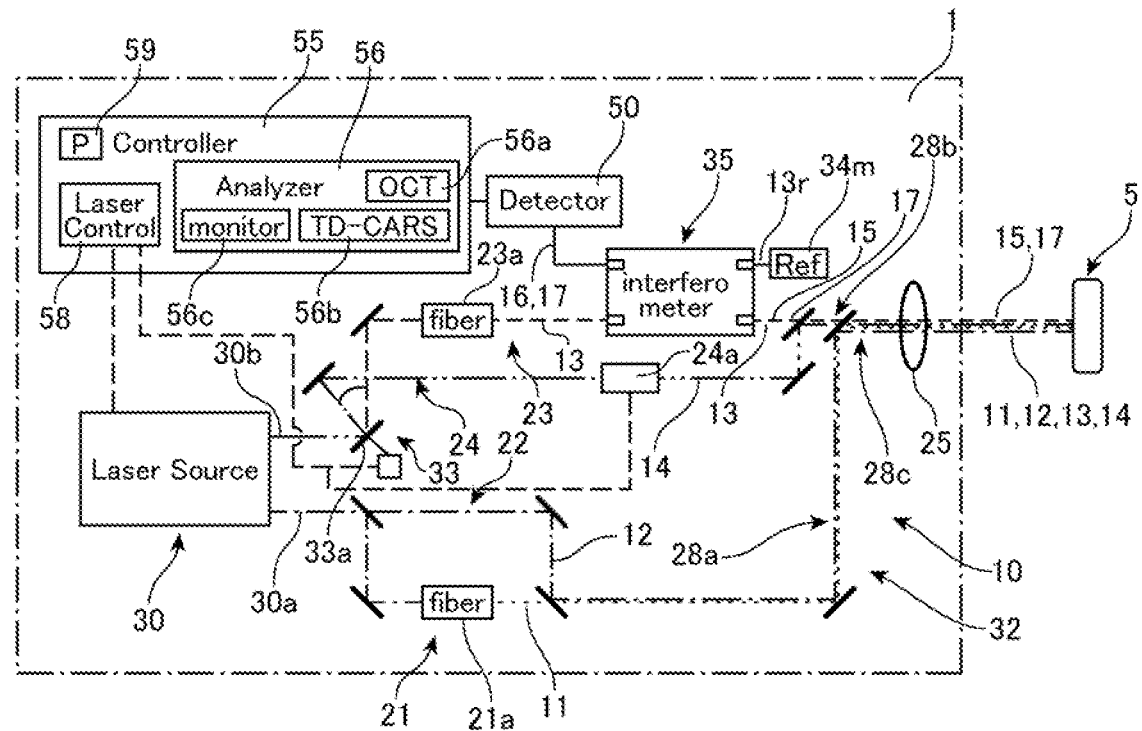
[Fig. 2]
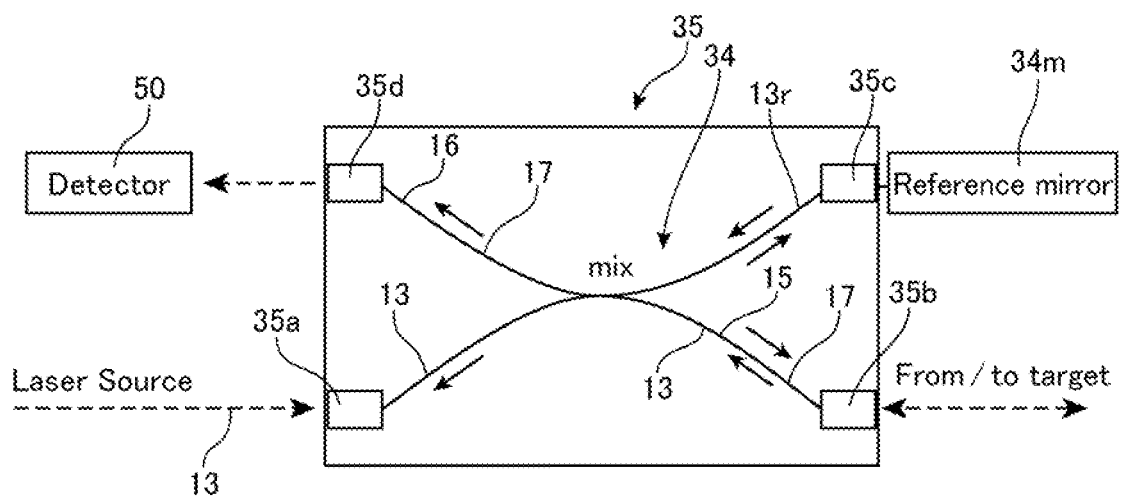

[Fig. 3]
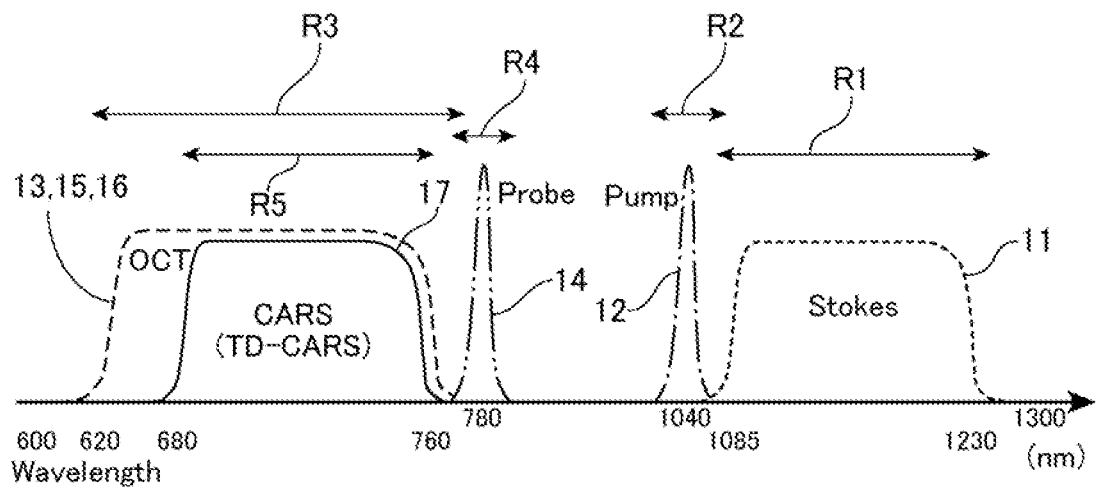
[Fig. 4]
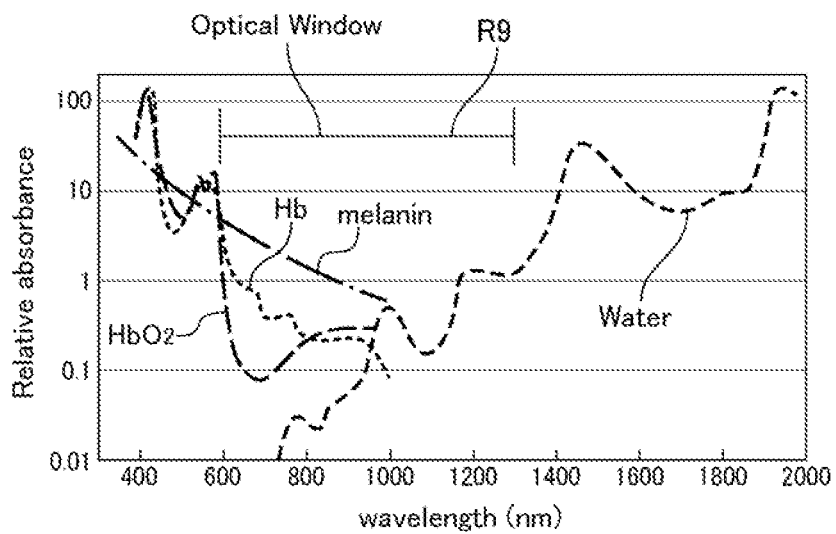

[Fig. 5]
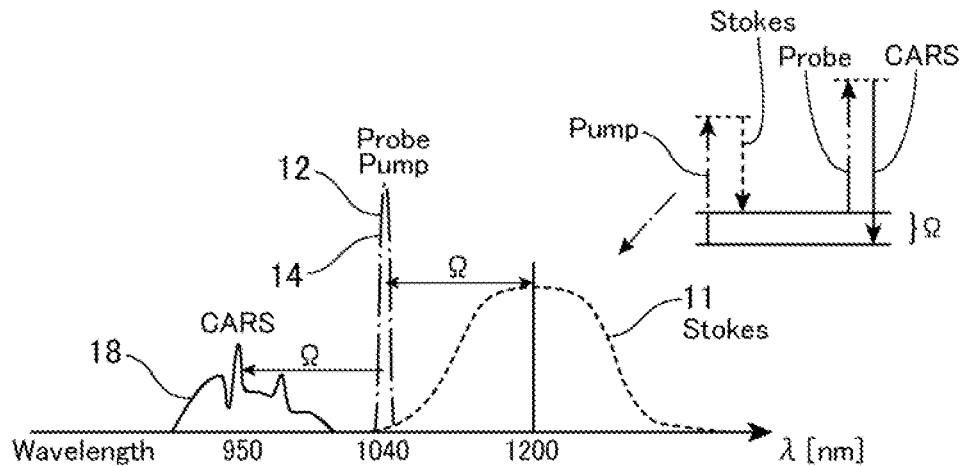
[Fig. 6]
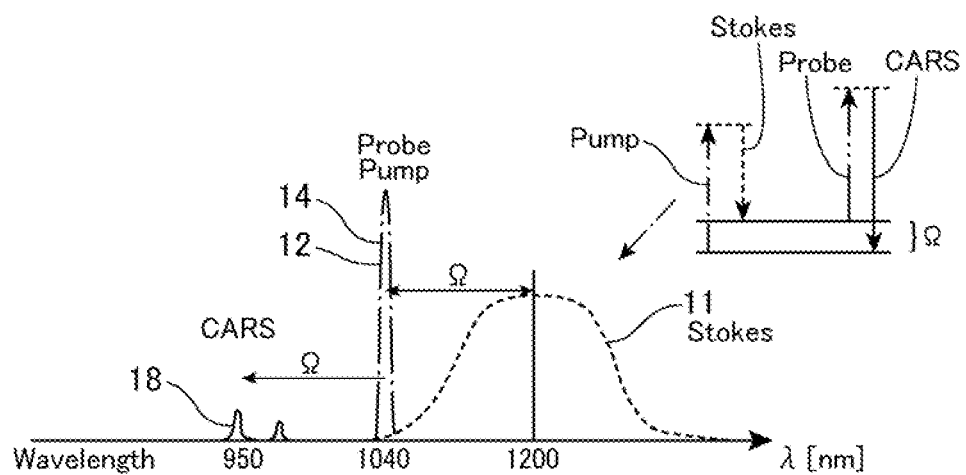

[Fig. 7]
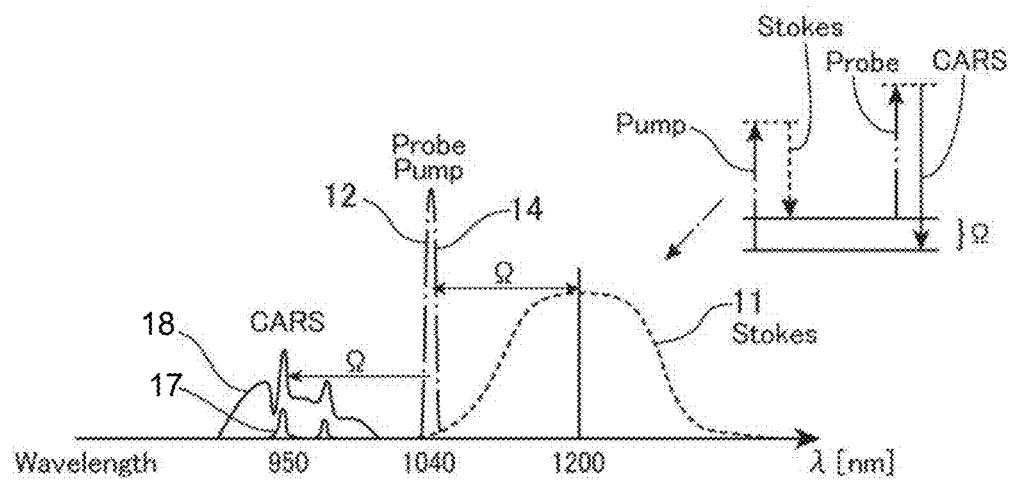
[Fig. 8]
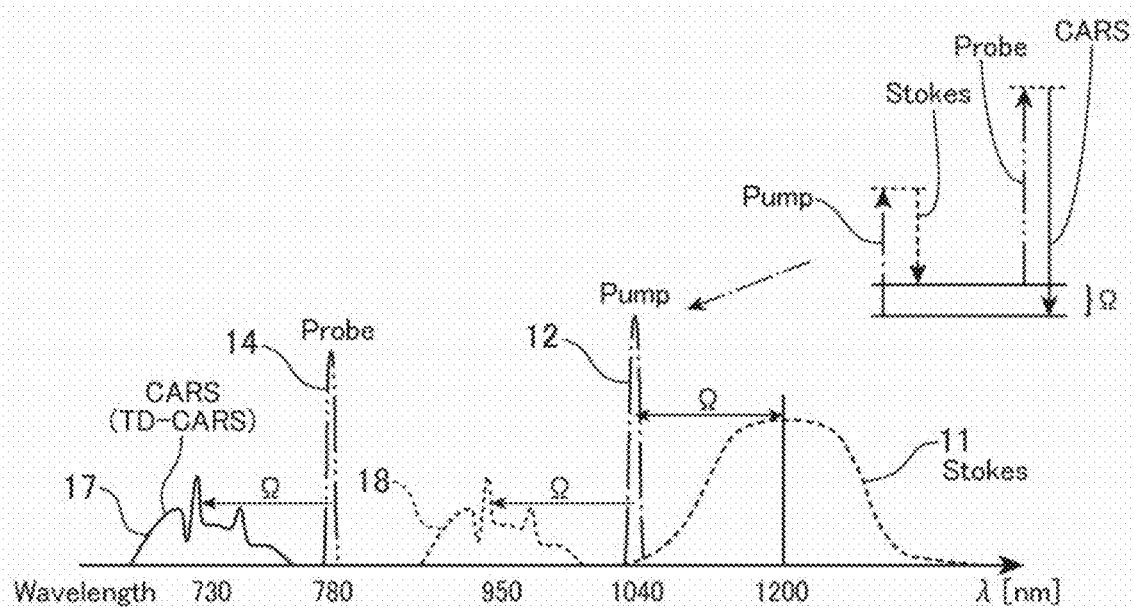

[Fig. 9]
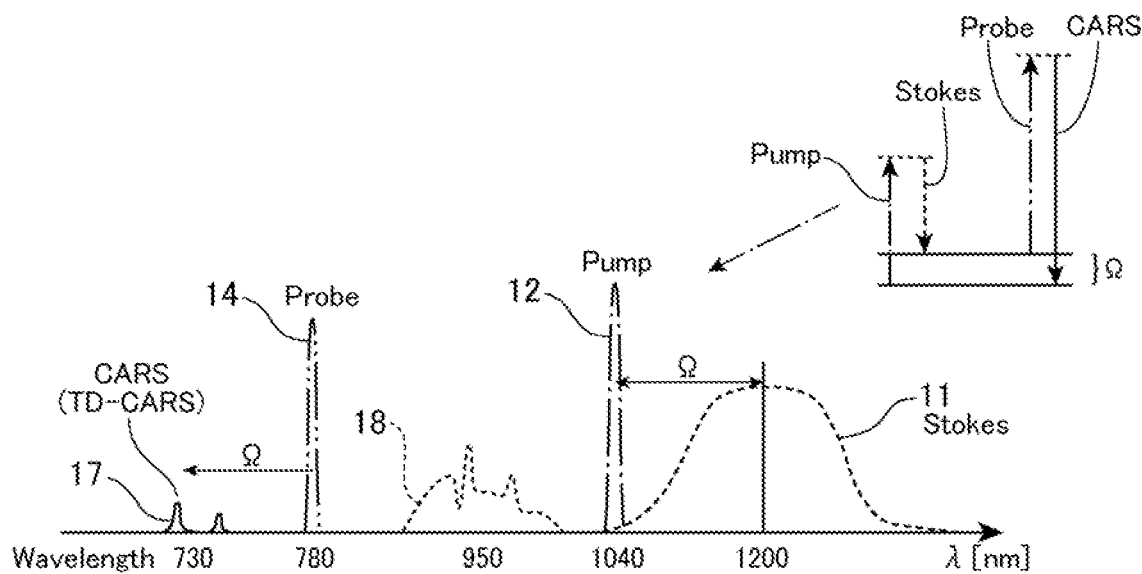
[Fig. 10]
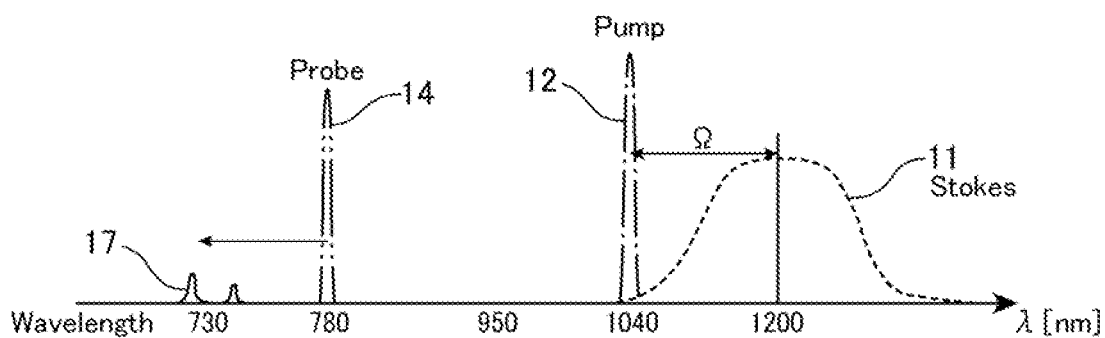

[Fig. 11]
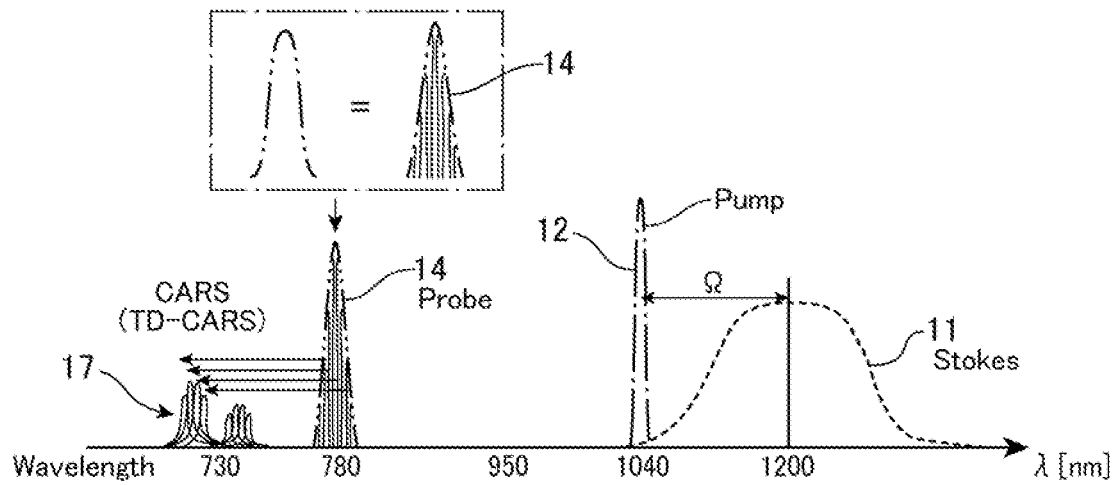
[Fig. 12(A)]
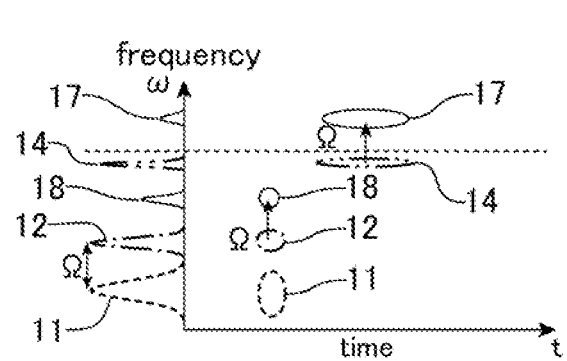
[Fig. 12(B)]
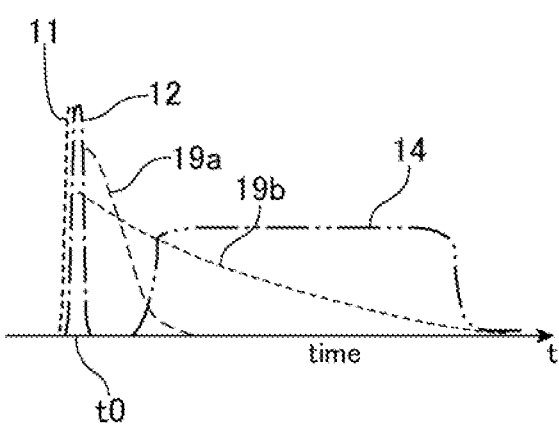

[Fig. 13(A)]
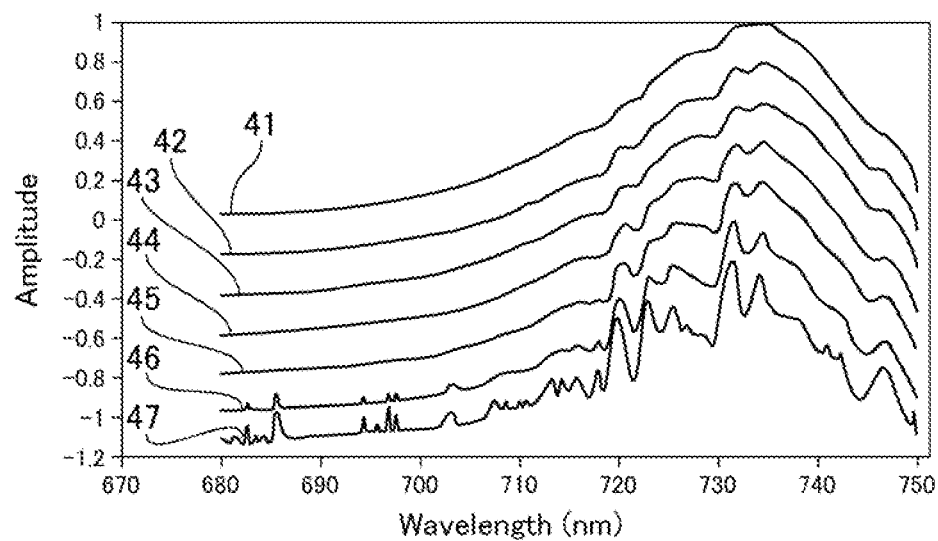
[Fig. 13(B)]
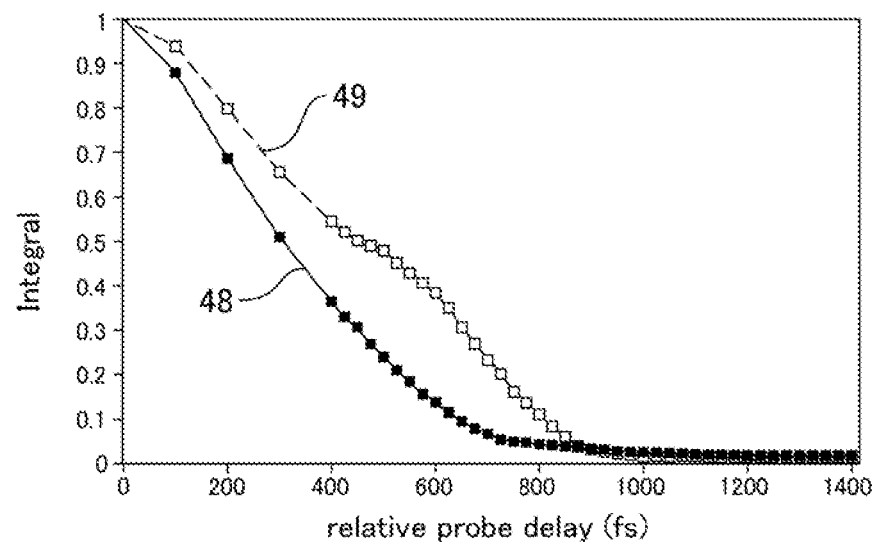

[Fig. 14]
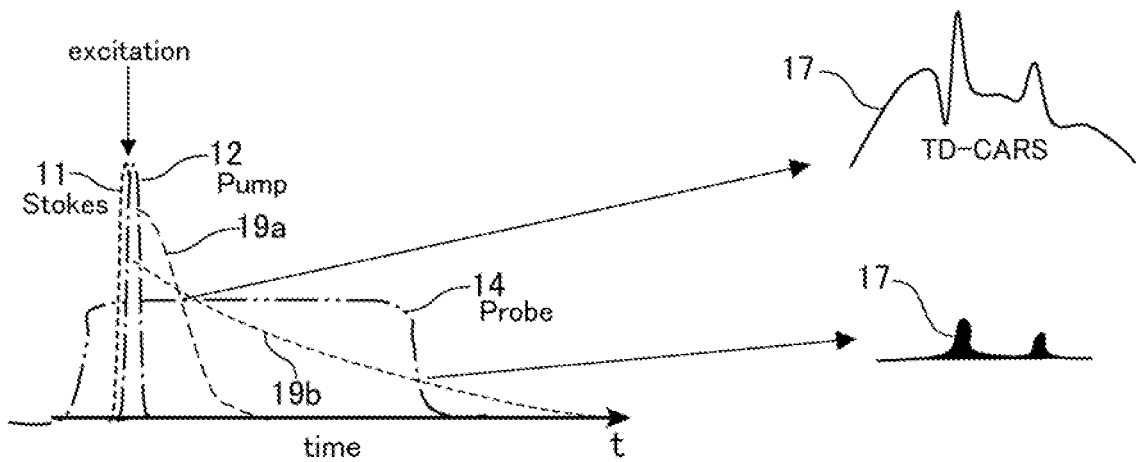
[Fig. 15]
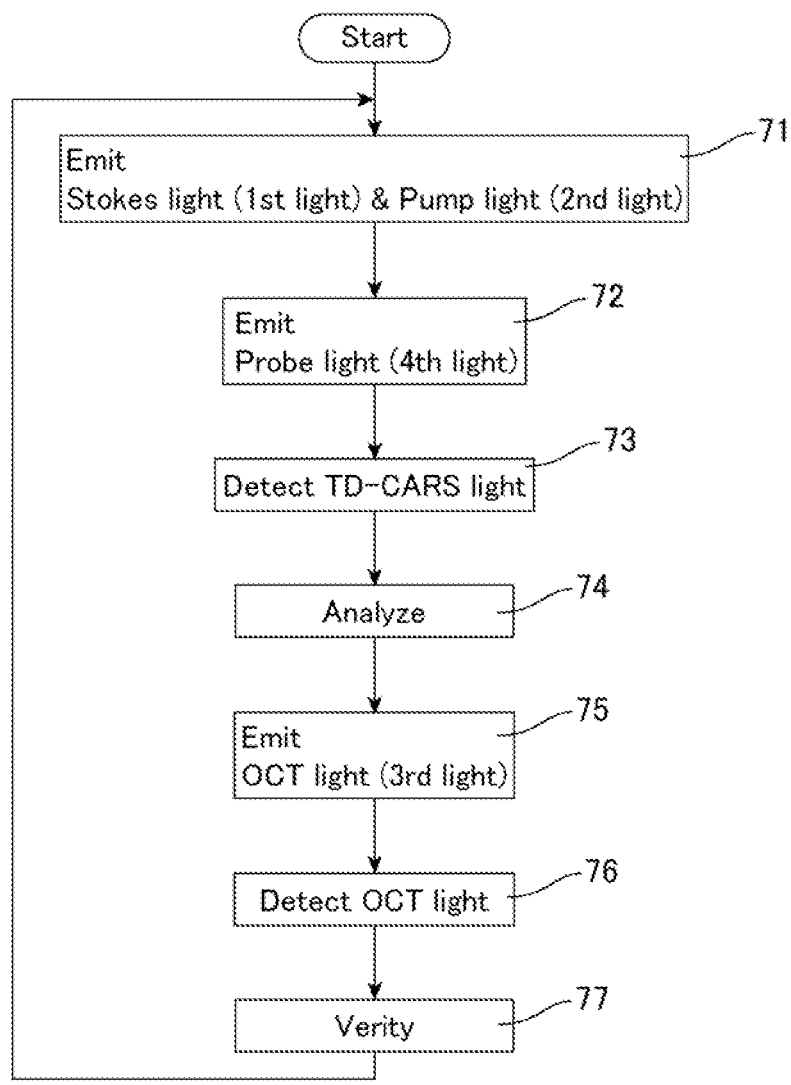

[Fig. 16]
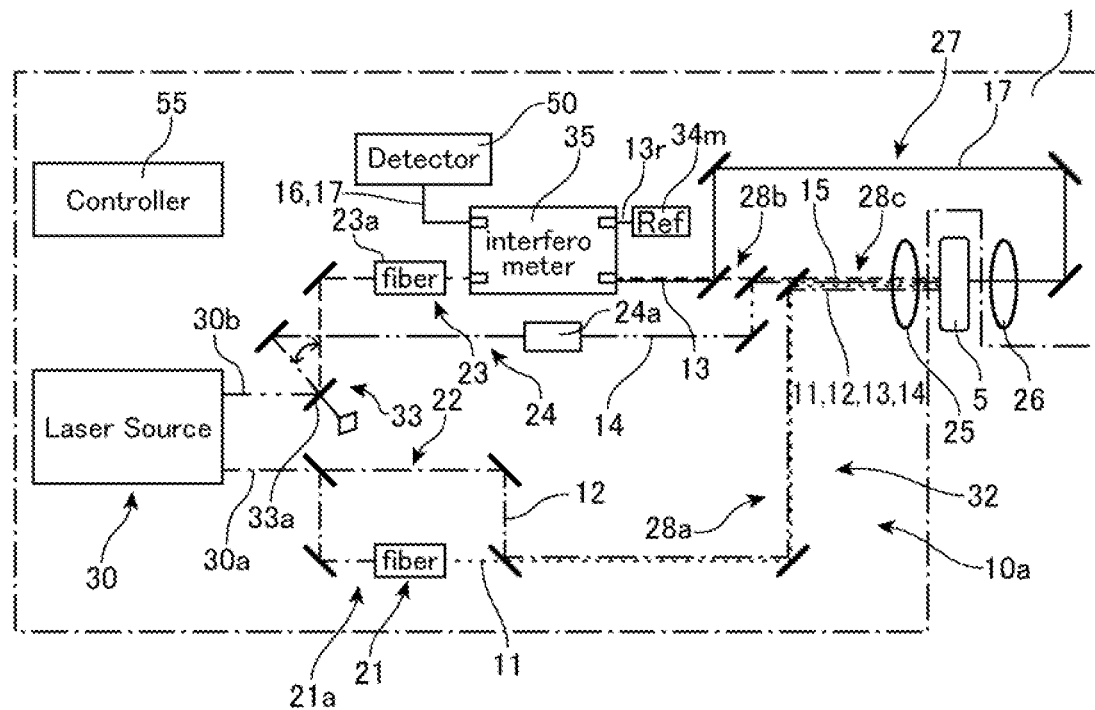
[Fig. 17]
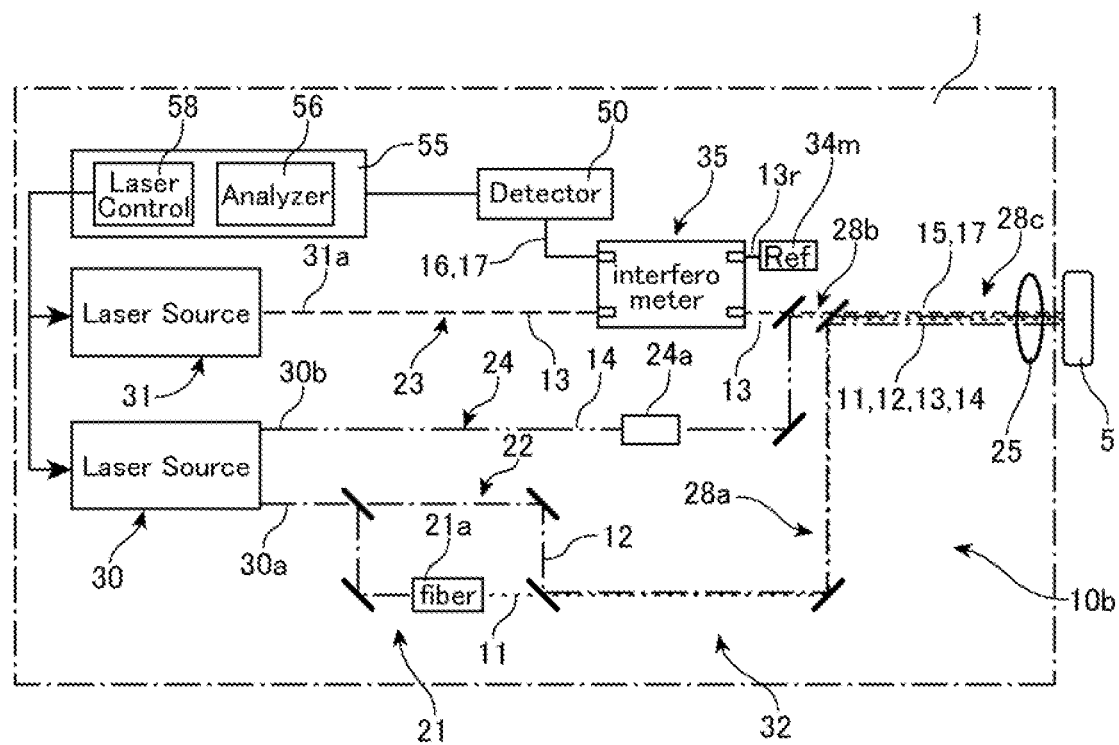

[Fig. 18]
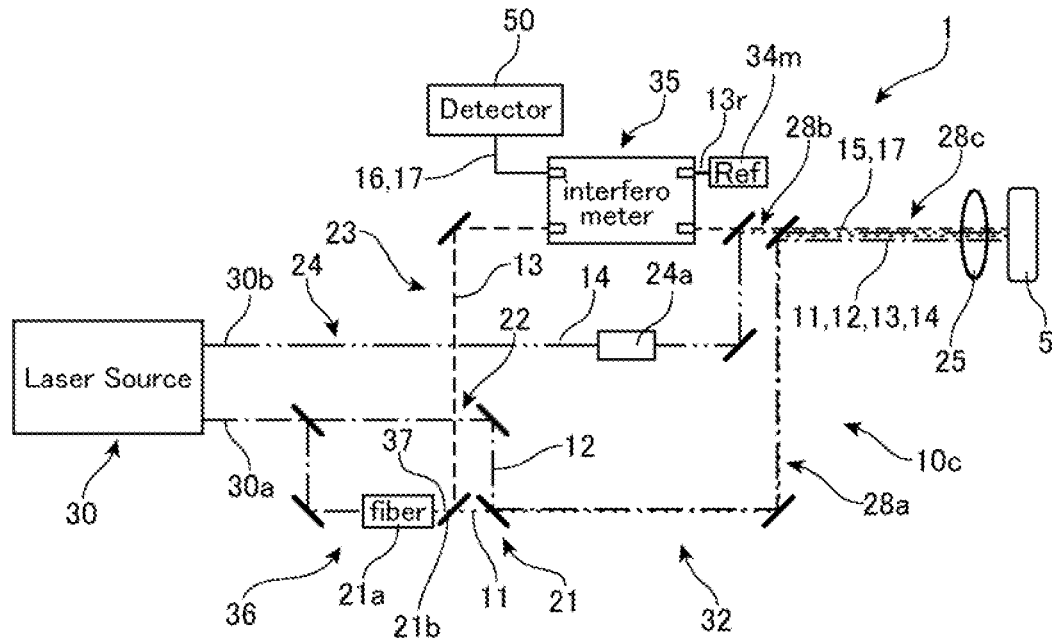
[Fig. 19]
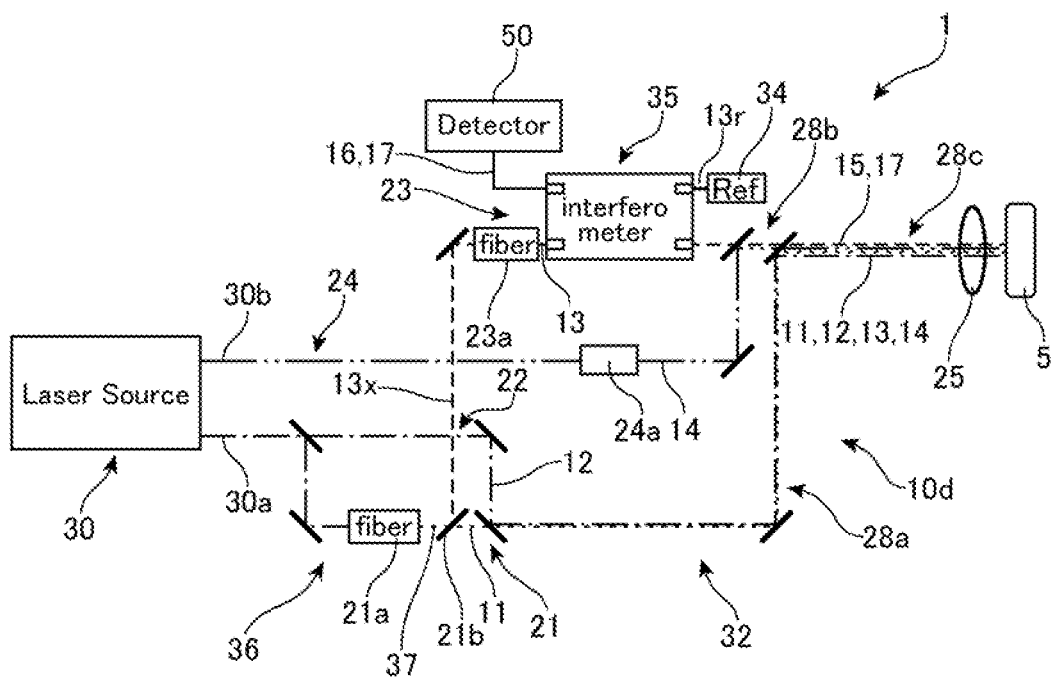

[Fig. 20]
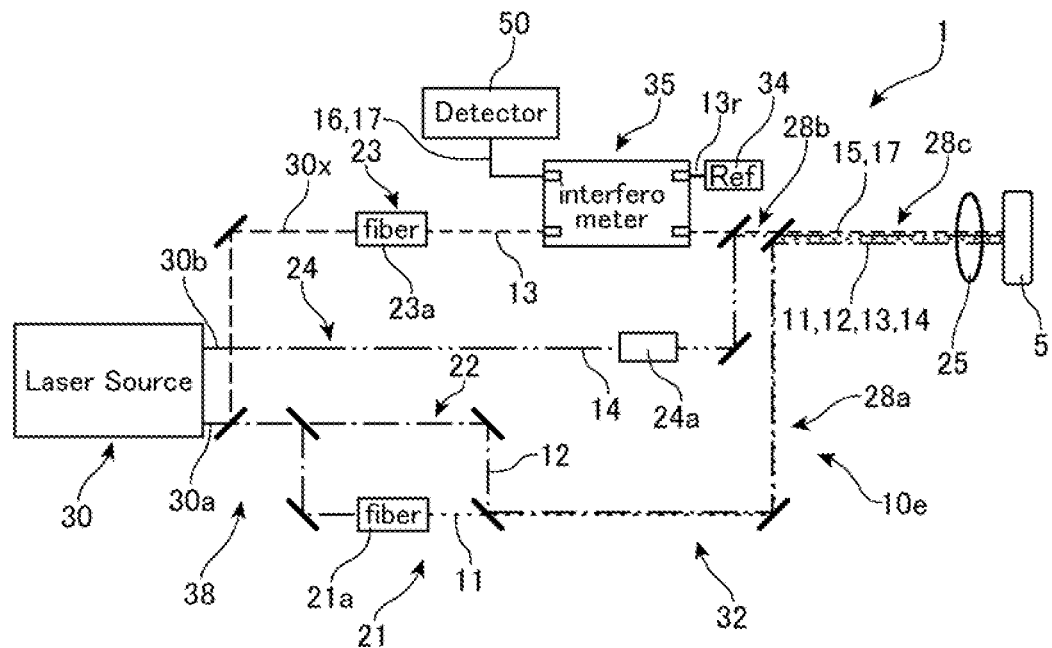
[Fig. 21]
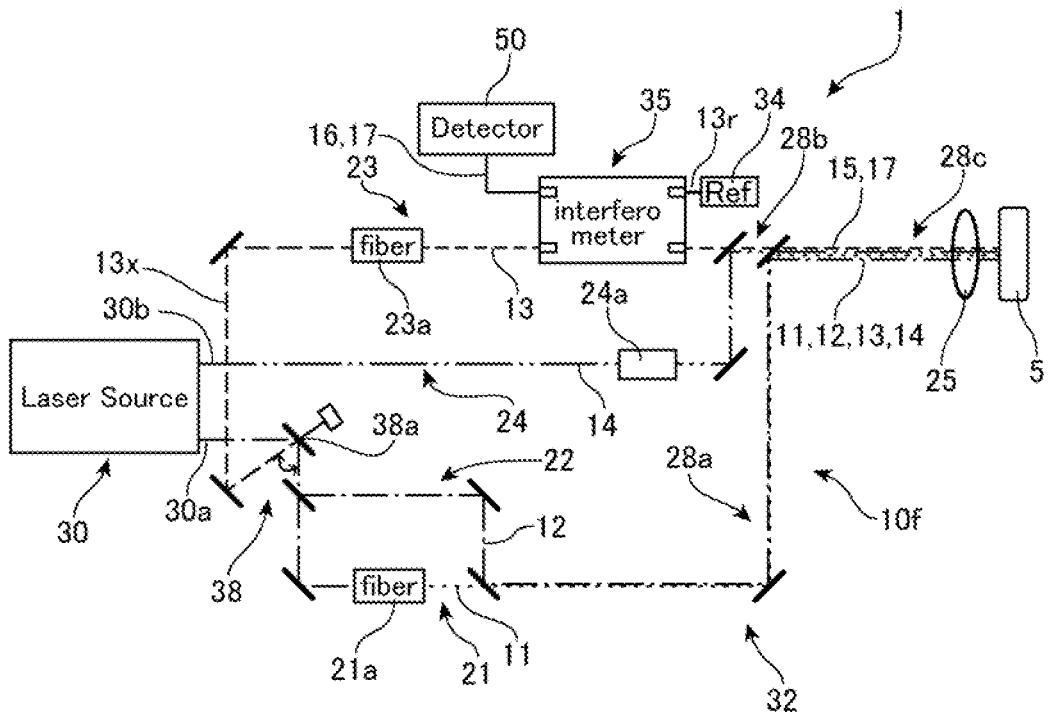

HYBRID OPTICAL SYSTEM

CROSS REFERENCE TO RELATED APPLICATIONS

The present invention is a continuation of U.S. patent application Ser. No. 17/420,152, which was filed on Jul. 1, 2021, which is a national stage application of PCT/JP2020/017447, which was filed on Apr. 23, 2020, which claims the benefit of U.S. Provisional Patent Application No. 62/840,001, which was filed on Apr. 29, 2019. The subject matter U.S. patent application Ser. No. 17/420,452: PCT/JP2020/017447 and U.S. Provisional Patent Application No. 62/840,001 are incorporated herein by reference.

TECHNICAL FIELD

The invention generally relates to a hybrid optical system that integrates Raman spectroscopy (RS) and optical coherence tomography (OCT).

BACKGROUND ART

In the publication WO2014/061147, a microscope is disclosed. The microscope includes: a first light dividing part that divides a light flux of light from a light source into a first pump light flux and a second pump light flux: a Stokes light source that receives the second pump light flux as an input and outputs a Stokes light flux: a multiplexing part that multiplexes the first pump light flux and the Stokes light flux to generate a multiplexed light flux: a first light-collecting part that collects the multiplexed light flux in a sample: a first detector that detects CARS light generated from the sample, the CARS light having a wavelength different from the multiplexed light flux: a second light dividing part that lets at least one of the second pump light flux and the Stokes light flux branch partially as a reference light flux: a second multiplexing part that multiplexes a light flux from the sample and the reference light flux to generate interfering light; and a second detector that detects the interfering light.

SUMMARY OF INVENTION

The present invention relates generally to a system that integrates Raman spectroscopy (RS) and optical coherence tomography (OCT) with a common detection system for both the RS and OCT, and more particularly to a system that integrates a Coherent Anti-Stokes Raman Scattering (CARS) and OCT. The system may be applicable to a system for biochemical and structural characterization of a target of interest of a living subject, and more particularly, for non-invasive evaluation of the biochemical compositions of a target of interest of a living subject and applications of the same.

Both optical imaging and spectroscopy have been applied to the non-invasive characterization of a target subject. Imaging techniques, such as OCT excel at relaying images of the target subject microstructure while spectroscopic methods, such as CARS, can probe the molecular composition of the target subject with excellent specificity.

OCT is a method of obtaining shape information, which reflects a change in the refractive index, using interference between a reflected light from an object (sample, target) and a reference light that has not irradiated the object. CARS is based on a nonlinear optical phenomenon where, when two light beams with different wavelengths are incident on an object, a CARS light that has a wavelength corresponding to the vibration of molecules forming the object is obtained. A plurality of different methods, such as transmissive CARS and reflective CARS, can be arranged regarding the direction of detecting a CARS light to the incident direction of a pump and a Stokes light.

CARS can obtain molecular information on a measurement target, and OCT can obtain shape information. Thus, the two techniques are in a mutually complementary relationship and a system integrating the CARS and the OCT with a compact size is important for use in many applications.

One of the aspects of this invention is a system comprising: a first optical path configured to supply a first light with a first range of wavelengths: a second optical path configured to supply a second light with a second range of wavelengths shorter than the first range of wavelengths: a third optical path configured to supply a third light with a third range of wavelengths shorter than the second range of wavelengths: an optical I/O unit configured to emit the first light, the second light and the third light to a target and acquire a light from the target: a reference unit configured to split off a reference light from the third light; and a detector including a range of detection wavelengths, wherein at least a part of the range of detection wavelengths is shared with a CARS light and an interference light, the CARS light is generated by at least the first light and the second light at the target and has a range of wavelengths at least partly overlapping with the third range of wavelengths, and the interference light is generated by the reference light and a reflected light from the target. The first light may be a Stokes light (Stokes beam), the second light may be a pump light (pump beam), and the third light may be a light (beam) for OCT.

Another aspect of this invention is a method comprising:
(i) emitting a first light with a first range of wavelengths and a second light with a second range of wavelengths shorter than the first range of wavelengths through an optical unit that is configured to output the first light and the second light to a target and acquire a light from the target;
(ii) detecting a CARS light, by a detector, generated by at least the first light and the second light at the target;
(iii) emitting a third light with a third range of wavelengths shorter than the second range of wavelengths through the optical unit to the target; and
(iv) detecting an interference light by the detector. The third range of wavelengths is at least partly overlapping a range of wavelengths of the CARS light, the interference light is generated by a reference light split off from the third light and a reflected light from the target, and the detector includes a range of detection wavelengths shared with the CARS light and the interference light.

In the above system and method, by using the third light (beam) having the wavelength range (third range) shorter than the wavelength range of the second light (pump light) and the first light (Stokes light) for OCT light, it becomes possible to obtain the interference light of OCT having the wavelength range (third range) shorter than the wavelengths of the first light and the second light, and the wavelength range (third range) of the interference light is at least partially overlapping with the wavelength range of CARS light. Therefore, a common detector that shares the range of detection wavelengths between CARS and OCT detection can be applied to simplify the system configuration and increase CARS detector's spectral resolution and OCT imaging depth. In this system and method, both CARS light and OCT signal may be going through the interferometer to hit the detector without re-routing the OCT signal after the interferometer to overlap with CARS light.

The system may include a fourth optical path configured to supply a fourth light (probe light, probe beam) with a fourth range of wavelength shorter than the second range of wavelengths and larger than or included in the third range of wavelengths for emitting via the optical I/O unit to generate the CARS (TD-CARS, time-delay CARS, time resolved CARS) light by the first light, the second light, and the fourth light. The CARS (TD-CARS) has a range of wavelengths at least partly overlapping the third wavelength range of the OCT signal and shorter than the fourth wavelength range. The fourth optical path may include a time delay unit configured to control a time difference between the emitting the fourth light and the emitting the second light. Also, the method may further include emitting a fourth light with a fourth range of wavelength shorter than the second range and larger than or included in the third range with a time difference from the emitting of the second light to generate the TD-CARS with a range of the wavelengths shorter than the fourth range and at least partly overlapping the third range.

Yet another aspect of this invention is a system comprising: a Stokes unit configured to supply a Stokes light with a first range of wavelengths for emitting to a target via an optical unit: a pump unit configured to supply a pump light with a second range of wavelengths shorter than the first range of wavelengths for emitting to the target via the optical unit: a probe unit configured to supply a probe light with a range of wavelength shorter than a range of wavelengths of a CARS light generated by the Stokes light and the pump light with a time difference from the emitting of the pump light, for emitting to the target via the optical unit; and a detector configured to detect a TD-CARS light with a range of wavelengths shorter than the fourth range generated by the Stokes light, the pump light, and the probe light at the target.

Yet another aspect of this invention is a method comprising: emitting a Stokes light with a first range of wavelengths and a pump light with a second range of wavelengths shorter than the first range of wavelengths to a target: emitting a probe light with a fourth range of wavelength shorter than a range of wavelengths of a CARS light generated by the Stokes light and the pump light with a time difference from the emitting of the pump light to the target; and detecting a TD-CARS light with a range of wavelengths shorter than the fourth range generated by the Stokes light, the pump light, and the probe light at the target.

The TD-CARS is generated by the Stokes light, the pump light, and the probe light at the wavelength range shorter than the fourth wavelength range of the probe light, and separated from the range of the CARS generated by the Stokes light and pump light. Therefore, the TD-CARS can be detected without the interference of the CARS.

Yet another aspect of this invention is a computer program for a computer to operate a device including a unit for emitting a light to a target via an optical unit and a detector for detecting a light from the target. The computer program includes executable codes for performing the steps of:

(a) emitting a first light with a first range of wavelengths and a second light with a second range of wavelengths shorter than the first range of wavelengths to the target via the optical unit;
(b) detecting a CARS light, by the detector, generated by at least the first light and the second light at the target;
(c) emitting a third light with a third range of wavelengths shorter than the second range of wavelengths to the target via the optical unit, a third range of wavelengths being at least partly overlapping a range of wavelengths of the CARS light; and
(d) detecting an interference light by the detector, wherein the interference light is generated by a reference light split off from the third light and a reflected light acquired through the optical unit.

A non-transitory computer readable medium storing the above program (program product, software) for controlling and operating the device, or detecting and analyzing using the device is also included in this invention.

BRIEF DESCRIPTION OF DRAWINGS

The embodiments herein will be better understood from the following detailed description with reference to the drawings, in which:

FIG. 1 illustrates an embodiment of a system including an optical system.
FIG. 2 shows optical paths in an interferometer.
FIG. 3 shows one of wavelength plans.
FIG. 4 shows an optical window for tissue.
FIG. 5 shows an example of a frequency domain of CARS signals.
FIG. 6 shows another example of a frequency domain of CARS signals.
FIG. 7 shows an example of TD-CARS signals and CARS signals.
FIG. 8 shows another example of a frequency domain of TD-CARS signals and CARS signals.
FIG. 9 shows yet another example of a frequency domain of TD-CARS signals and CARS signals.
FIG. 10 shows a frequency domain with narrow probe bandwidth.
FIG. 11 shows a frequency domain with broader probe bandwidth.
FIGS. 12(A) and 12(B) show a time domain with Stokes light, Pump light, and Probe light.
FIGS. 13(A) and 13(B) show examples of TD-CARS spectra.
FIG. 14 shows another time domain with Stokes light, Pump light, and Probe light.
FIG. 15 shows a flow diagram of a process in this system.
FIG. 16 shows another embodiment of the optical system.
FIG. 17 shows yet another embodiment of the optical system.
FIG. 18 shows yet another embodiment of the optical system.
FIG. 19 shows yet another embodiment of the optical system.
FIG. 20 shows yet another embodiment of the optical system.
FIG. 21 shows yet another embodiment of the optical system.

DESCRIPTION OF EMBODIMENTS

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

FIG. 1 illustrates a system 1 including a hybrid optical system 10 according to an embodiment. The system 1 includes the hybrid optical system 10 and a controller 55. The hybrid optical system 10 uses OCT (Optical Coherence Tomography) and CARS (Coherent Anti-Stokes Raman Scattering) to acquire data indicative of surface and internal conditions and components of a target 5 such as a human body. The controller 55 includes an analyzer 56 that verifies (confirms) the state of the target 5 by OCT and analyzes internal compositions (components) by CARS.

The hybrid optical system (optical system) 10 includes a laser source 30 for generating a first laser 30a with a first wave length 1040 nm for a Stokes light (Stokes beam, Stokes pulse, a first light) 11 and a pump light (pump beam, pump pulse, second light) 12, a second laser 30b with a second wavelength 780 nm, an OCT light 13, and a probe light (probe beam, fourth light) 14. One of preferable laser source 30 is a fiber laser. The first laser 30a may include one to several hundred fS (femtosecond)-order pulses with tens to hundreds of mW. The second laser 30b may include one to several tens pS (pico second)-order pulses with tens to hundreds of mW, and the second laser 30b with the wavelength of 780 nm may be generated from the source oscillator with a wavelength of 1560 nm.

The optical system 10 includes a plurality of optical elements 32 such as filters, mirrors, dichroic mirrors and prisms for arranging optical paths to separate and combine the leaser lights. The optical system 10 includes a Stokes light path (first optical path, Stokes unit) 21 that is configured to supply the Stokes light (first light) 11 with a first range R1 of wavelengths 1080-1300 nm from the first laser 30a which is common to the pump light 12, through the PCF (Photonic Crystal Fiber, fiber) 21. The optical system 10 includes a pump light path (second optical path, pump unit) 22 that is configured to supply the pump light (second light) 12 with a second range R2 of wavelengths 1070 nm that is shorter than the first wavelength range (first range) R1 from the first laser 30a which is common to the Stokes light 11. The optical system 10 includes a common optical path 28a that supplies the Stokes light 11 provided by the 21 and the pump light 12 provided by path 22 to the optical I/O unit 25. The optical path 21, 22, and 28a include necessary optical elements 32 such as filters, fibers, dichroic mirrors and prisms to configure each optical path. The same applies to the optical paths described below.

The optical system 10 further includes an OCT light path (third optical path) 23 that is configured to supply an OCT light (third light) 13 with a third range R3 of wavelengths 620-780 nm shorter than the second wavelength range R2 from the second laser 30b that is common to the probe light 14, through a fiber 23a. The optical system 10 further includes a probe light path (fourth optical path, probe unit) 24 that is configured to supply the probe light (probe beam, probe pulse, fourth light) 14 with a fourth range R4 of wavelength of 780 nm that is shorter than the second wavelength range R2 and larger than or included in the third wavelength range R3 from the second laser 30b that is common to the OCT light 13. The optical system 10 includes a common optical path 28b that supplies the OCT light 13 provided by the path 23 via an interferometer 35 and the probe light 14 provided by path 24 to the optical I/O unit 25.

The probe light path 24 includes a time delay unit 24a that is configured to control a time difference between emission of the probe light (fourth light) 14 and emission of the pump light (second light) 12. The time delay unit may have collimators and a motorized delay stage that can control the distance between the collimators. Time delay may be controlled by the laser control unit 58 in the controller 55. By using the time delay unit 24a, the probe light path 24 can supply the probe light 14 with a time difference from the emitting of the pump light 12 for emitting to the target 5 via the optical I/O unit 25.

The optical system 10 further includes the optical I/O unit (optical unit) 25 that is configured to coaxially output the Stokes light 11, the pump light 12, the probe light 14, and the OCT light 13 to the target 5 and acquire a light from the target via a common light path 28c. A typical optical I/O unit 25 is an objective lens or lens system that faces to the target 5 and, through the lens 25, the Stokes light 11, the pump light 12, and the probe light 14 are emitted or irradiated to the target 5 and the CARS light (TD-CARS light) 17 is acquired or received from the target 5. Also, through the lens 25, the OCT light 13 is emitted or irradiated to the target and a reflected light 15 is acquired or received from the target 5. Hence, the optical system 10 gets a backward CARS light (Epi-CARS) 17 and includes the first input optical path 28c that is configured to guide the backward CARS light 17 from the optical I/O unit 25.

FIG. 2 shows an example of an interferometer 35. The interferometer 35 includes a reference unit 34 that is configured to split off a reference light 13r from the OCT light 13 with a reference mirror 34m. The fiber interferometer 35 includes four arms (light paths) to separate and mix the lights. For the OCT light 13, a part of the inputted light from a port 35a is separated as the reference light 13r to the reference mirror 34m via a port 35c and the other part is outputted to the sample (object, target) 5 via a port 35b. The returned (reflected) OCT light 15 from the target 5 is inputted via the port 35b, combined or multiplexed with the reference light 13r to generate the interference light 16. The interference light 16 is outputted to a detector 50 via a port 35d. The CARS light 17 is also supplied to the detector 50 through the interferometer 35 using the port 35b and 35d.

In the optical system 10, using the optical paths above, in order from the laser source 30 side, the OCT light 13 is combined with the probe light 14, the combined light is further combined with the Stokes light 11 and the pump light 12, then through the optical I/O unit 25 such as the object lens (lens system), the combined light is emitted to and irradiated on the target 5 such as a skin of human. The reflected or generated light (the reflected light 15 and the CARS light 17) from the target 5 is acquired through the object lens of the optical unit 25 and goes back to the paths of the optical system 10.

The optical element such as a dichroic mirror for combining the OCT light 13 and the probe light 14 may be a separator or selecting unit that is configured to select a reflected light 15 of the OCT light having 620-780 nm and a CARS light. In this system 10, a TD-CARS light 17 with a range R5 of wavelengths of 680-760 nm that is shorter than the wavelength range R4 and is at least partly overlapping the third wavelength range R3 is filtered from the acquired light and supplied to the detector 50. The TD-CARS light 17 is generated by the Stokes light 11, the pump light 12, and the probe light 14 at the target 5. Both the TD-CARS light 17 and the interference light 16 are supplied to the detector 50 through the interferometer 35 in this optical system 10, but other optical paths for making the interference light 16 and supplying the interference light 16 and the TD-CARS light 17 to the detector 50 may be provided in the optical system 10.

The detector 50 of the optical system 10 includes a range DR of detection wavelengths shared with the TD-CARS light 17 and the interference light 16. Typically, the detector 50 may have the same detection range (measurement rage) DR as the larger one of the wavelength range R3 of the OCT light 13 and the wavelength range R5 of the TD-CARS light 17. For example, in this optical system 10, the TD-CARS light 17 is the detection target and it has a range R5 of wavelengths of 680-760 nm, therefore the OCT light 13 with a third range R3 of wavelengths 620-780 nm is applied and the detection range DR could be set to cover the range of wavelengths 620-780 nm or over. By applying the single and common detector 50 that shares the range DR of detection wavelengths between CARS and OCT detection, the system configuration becomes simplified, and CARS detector's spectral resolution and OCT imaging depth are increasing. When the CARS light generated by the Stokes light 11 and the pump light 12 (using the probe light with the same wavelength range R2 of that of the pump light 12) is the detection target, since the CARS light has a range of wavelengths about 900-1000 nm that is shorter than the wavelength range R2, the OCT light 13 with a range of wavelengths exceeding 900-1000 nm is applied and the detection range DR could be set to cover the range of wavelengths of OCT light, for example 800-1000 nm. In any case, the detection wavelength range DR of the detector 50 is set below the second wavelength range R2. In this optical system 10, the time-division scan may be required because the CARS light 17 and OCT light 13 use the same spectral range of the single detector 50.

The optical system 10 further comprises an optical element 33a for switching generating or supplying the CARS light 17 and the interfering light 16 in a time-division manner. The optical system 10 further comprises a generating optical path 33 that is configured to generate at least one of the OCT light (third light) 13 and the probe light (the fourth light) 14 from the second laser light (common light source) 30b, and the optical path 33 includes the optical element (switching unit) 33a to generate by switching between the OCT light (third light) 13 and the probe light (fourth light) 14. The optical element 33a may be a MEMS mirror that changes the direction of the source laser 30b to the probe light path 24 and the OCT light path 23 under control of a laser control unit 58 in the controller 55. All of the incoming light to the optical element 33a can be used for either generating CARS 17 or OCT light 13 by diverting it with a moveable mirror 33a. In this optical system, the OCT light 13 is generated from the same source as the probe light 14, and OCT light generation is independent of Stokes generation, which makes it more flexible and easier to achieve a good spectrum for the OCT light 13, but PCFs 23a and 21a are required for OCT light generation and Stokes light generation respectively.

In this optical system 10, by cutting the probe light 14 using the optical element 33a, the TD-CARS light 17 with the range R5 is not generated at the target 5, only a CARS light with the longer range of wavelengths than the range R3 is generated by the Stokes light 11 and the pump light 12 as described later, and the CARS light generated by only the Stokes light 11 and the pump light 12 is not detected by the detector 50 of this optical system 10. The analyzer 56 in the controller 55 can grasp whether the signal from the detector 50 is OCT or TD-CARS in synchronization with the switching of the optical element 33 and analyze each signal properly.

The conventional system for combining a CARS microscope with OCT uses two detectors or uses one detector splitting into one half for CARS and the other half for OCT for detection. That is because the CARS light and OCT light have different spectral ranges. A system using two detectors becomes complex and large, and a system using single detector reduces spectral resolution for CARS and the imaging depth for OCT. The system 1 shown in FIG. 1 uses one single detector 50 but with the (nearly) same spectral range for CARS and OCT. When using a single detector 50, it may be possible to re-route the OCT signal (interference light) 16 after the interferometer 35 to overlap with TD-CARS light 17 and hit the single detector 50. In this optical system 10, both TD-CARS 17 and OCT signal (reflected light) 16 are going through the interferometer 35.

FIG. 3 shows one of the wavelength plans of this optical system 10. The optical system 10 should satisfy requirements for several operating modes with minimal hardware and cost. One of the requirements for this optical system 10 may be that CARS emissions must not overlap TD-CARS emissions. Another one of requirements for this optical system 10 may be that TD-CARS emissions must overlap OCT excitation for a shared spectrometer range. Yet another one of requirements for this optical system 10 may be that excitation must have good efficiency through tissue as shown in FIG. 4.

FIG. 4 shows one of the optical windows R9 for tissue that is effective for detecting the internal state of living body such as human body. FIG. 4 depicts the relative absorbances of major materials of living body such as water, melanin, reduced hemoglobin (Hb), and oxygenated hemoglobin ($HbO_2$). The light with the range of wavelengths 600 nm to 1300 nm is hard to be absorbed and suitable for measurement of living body. From the view point of the optical window shown in FIG. 4, the Stokes light 11 with the first range R1, the pump light 12 with the second range R2, the probe light 14 with the fourth range R4, and the OCT light 13 and the TD-CARS light 17 with the third range R3 and R5 should be arranged in the range of the optical windows between 600 nm to 1300 nm.

In the plan shown in FIG. 3, Stokes light 11 has the first range R1 of wavelengths 1085-1230 nm (400 $cm^{-1}$~1500 $cm^{-1}$), Pump light 12 has the second range R2 of wavelengths 1040 nm, Probe light 14 has the fourth range R4 of the wavelengths 780 nm, OCT light 13 has the third range R3 of wavelengths 620-780 nm, and TD-CARS light 17 has the range R5 of the wavelengths 680-760 nm. The all of ranges R1, R2, R3, R4 and R5 are included in the range of wavelengths 600 nm to 1300 nm. The second range R2 is shorter than the first range R1, the third range R3 is shorter than the second range R2, the fourth range R4 is shorter than the second range R2 and larger than or included in the third range R3, and the range R5 of TD-CARS 17 is shorter than the fourth range R4 and at least partly overlapping the third range R3.

FIGS. 5-7 show wavelength plans when the probe light (time delayed probe) 14 having the same wavelength, for example 1040 nm, of the pump light (non-delayed probe) 12 is applied. Since the TD-CARS 17 due to the probe light 14 is generated on the same range of the CARS 18 only generated by the Stokes light 11 and the pump light 12 at the wavelengths corresponding to the molecular vibration Ω from the wavelength of pump light 12, the TD-CARS signals 17 are interfered or embedded in the CARS signals 18 and cannot be distinguished from the CARS signals 18. Accordingly, the time-delayed signal has to be generated at a different frequency and the probe pulse 14 needs to be shifted.

FIGS. 8 and 9 show wavelength plans when the probe light 14 having the shorter wavelength range R4, for example 780 nm, than the range R2 of the pump light 12 is applied. The TD-CARS 17 having the wavelength range R5 shorter than the range R4 of the probe light 14 is generated. That is, by using the probe light 14 with the range R4 of wavelengths shorter than the range of wavelengths of the CARS light only generated by the Stokes light 11 and the pump light 12 with a time difference from the emission of the pump light 12, the TD-CARS 17 having the wavelength range R5 shorter than the wavelength range of the CARS light 18 is generated. Accordingly, no interference is made between the TD-CARS 17 and the CARS 18, and distinct TD-CARS 17 can be detected without interference with the CARS light 18. The probe light 14 with the range of wavelength shorter than the range of wavelengths of a CARS light 18 only generated by the Stokes light 11 and the pump light 12 may be required to detect a time difference CARS (TD-CARS) 17 that is generated by the Stokes light 11, the pump light 12 and the probe light 14.

FIG. 10 shows a distinct TD-CARS spectrum 17 by the probe light 14 with narrow bandwidth, and FIG. 11 shows a broader TD-CARS spectrum 17 due to the broad probe light 14. In the frequency domain, the probe wavelength R4 has to be shifted by a certain minimum amount from the pump wavelength 12. As is clearly shown in the Figures, a narrow probe bandwidth generates distinct spectrum. Broad probe implies as combination of several narrow frequency components and each frequency component generates the same spectrum but at a different position. Hence, smooth spectrum has washed out features, and spectral resolution is lost. The probe light 14 needs to have a narrow bandwidth R4 to assure optimum spectral resolution in the order of the linewidth of the molecule's resonances. Since typical Raman linewidth is approx. 5-15 $cm^{-1}$, the probe bandwidth R4 therefore also be ~15 $cm^{-1}$. In the time domain, the probe light 14 may have a time width in the order of a few pico-seconds duration to separate excitation and probing in time. Pump light 12 and Stokes light 11 have to be in the fs regime, for example, Pump light 12 and Stokes light 11 may have duration roughly below 200 fs.

FIG. 12(A) shows a time domain of Stokes light 11, pump light 12, and probe light 14. FIG. 12(A) also includes the signal (CARS light) 18 from pump light 11 and the signal (TD-CARS light) 17 from delayed probe light 14. Delayed probe light 14 with higher frequency and narrow spectrum may be required to get distinct TD-CARS signal 17.

FIG. 12(B) shows how the TD-CARS signals work. At the time t0, the Stokes light 11 and the pump light 12 are excited in fs order. A line 19a shows an electronic response (NRB, negative response bias) and a ling 19b shows a vibrational response. By using time delayed probe signal 14, vibrational responses can be detected as the TD-CARS signal 17.

FIG. 13(A) shows examples of TD-CARS spectra with varying delay time (time difference). FIG. 13(A) depicts spectra of high concentration glucose solution, the line 41 shows a spectrum without delay, the line 42 shows a spectrum with 400 fs (femtosecond), the line 43 shows a spectrum with 600 fs, the line 44 shows a spectrum with 750 fs, the line 45 shows a spectrum with 850 fs, the line 46 shows a spectrum with 950 fs, and the line 47 shows a spectrum with 1025 fs.

FIG. 13(B) shows total signal drop-off of the TD-CARS signal 17. The line 48 shows a signal with 621-635 nm, and the line 49 shows a signal with 685-745 nm. As is shown in the figures, probe delay leads to slowly decreasing signal and improving contrast due to quicker decay of NRB. Glucose peak is clearly enhanced with increasing probe delay. The probe pulse 14 that may be a pico-second pulse may be generated from the end or nearly end of the electronic response to separate the vibration response from the non-resonant component.

FIG. 14 depicts another embodiment of the probe light 14. The probe pulse 14 may be generated and emitted prior to or at the same time of that of the Stokes light 11 and pump light 12 till the duration of vibration response. FIG. 15 is a flow diagram (flowchart) that illustrates a process performed by the system 1. In this embodiment, a program (program produce, software, application) 59 stored in the memory of the controller 55 is provided for running the process on the controller 55 with computer resources such as the memory, CPU, and others. The program (software) 59 may be provided as other memory medium readable by a processor or a computer.

At step 71, the laser controller 58 controls the laser source 30 and the optical system 10 to emit the Stokes light (first light) 11 with the first range R1 of wavelengths and the pumps light (second light) 12 with a second range R2 of wavelengths shorter than the first wavelength range R1 through the optical I/O unit (optical unit) 25. At step 72, the laser controller 58 controls the laser source 30 and the optical system 10 to emit the probe light (fourth light) 14 with the fourth range R4 of wavelength with a time difference from the emitting of the pump light 12. At the step 72, the probe light 14 may be emitted to the target 5 varying the time difference from the emitting of the pump light using the time delay unit 24a.

At step 73, the detector 50 detects a TD-CARS light generated by the Stokes light 11, the pump light 12, and the probe light 14 at the target 5. At step 74, a TD-CARS analyzing module 56b of the analyzer 56 may analyze at least a part of compositions of a part of the target 5 using detection results of the TD-CARS light 17.

At step 75, before or after the step 74 or in parallel, the laser controller 58 controls the laser source 30 and the optical system 10 to emit the OCT light 13 (third light) with the third range R3 of wavelengths in time division from the probe light 14 through the optical unit 25 to the target 5. At step 76, the detector 50 detects the interference light 16 generated by the reference light 13r and the reflected light 15 from the target 5 in time division from the TD-CARS light 17 since the third range R3 of the interference light 16 is at least partly overlapping the range R5 of the TD-CARS light 17 and the detector 50 includes the range of detection wavelengths shared with the TD-CARS light 17 and the interference light 16.

At step 77, an OCT analyzing module 56a of the analyzer 56 may generate OCT images from the interference light 16 detected by the detector 50 and a monitoring module 56c of the analyzer 56 may verify the part of target 5 at which the TD-CARS light 17 is generated, for confirming the reliability of information by the TD-CARS light 17 and analyzing the target 5 in cooperation with the information of the OCT images and the information of the TD-CARS light.

FIG. 16 shows another embodiment of the system 1 including an optical system 10a. This optical system 10a includes an optical input unit 26 arranged on an opposite side of the target (sample) 5 from the optical I/O unit 25 and a second input optical path 27 that is configured to guide the CARS light (forward TD-CARS light) 17 from the optical input unit 26 to the common light path 28b shared with the OCT light 13 and reflected light 15. Other optical paths and elements of the optical system 10a depicted in this figure are common to those of the optical system 10 depicted in FIG. 1.

FIG. 17 shows yet another embodiment of the system 1 including an optical system 10b. The optical system 10b includes a laser source 31 that is configured to supply the OCT light 13 with the wavelength range R3 independently from the lights for making the TD-CARS 17. The laser source 31 may output a laser light 31a with the wavelength range R3 and may include the fiber 24a for extending or broadening the wavelength range. The laser source 30 for outputting the Stokes light 11, the pump light 12, the probe light 14, and the laser source 31 for outputting the OCT light 13 may be controlled to emit each laser light in time division or alternatingly by the laser control unit 58 in the controller 55. The optical element 33a for switching the laser light 30b to supply the probe light 14 and the OCT light 13 may not be required. Other optical paths and elements of the optical system 10b are common to those of the optical system 10 depicted in FIG. 1.

FIG. 18 shows yet another embodiment of the system 1 including an optical system 10c. This optical system 10c comprises a generating optical path 36 that is configured to generate the OCT light (third light) 13 from the light source 37 common to the Stokes light (first light) 11. In this optical system 10c, the PCF 21a extends the laser light 30a to cover the width of wavelength ranges R1 for the Stokes light 11 and R3 for the OCT light 13 and a dichroic mirror 21b separates the OCT light 13 to the OCT light path 23.

FIG. 19 shows yet another embodiment of the system 1 including an optical system 10d. This optical system 10d includes a generating optical path 36 that is configured to generate the OCT light (third light) 13 from the light source 37 common to the Stokes light (first light) 11. In this optical system 10d, the PCF 21a extends the laser light 30a to cover the range R1 of the Stokes light 11 and a dichroic mirror 21b separates the light 13x around 850 nm to the OCT light path 23 to be an input for the second fiber 23a to make the OCT light 13 with the range R3. In this optical system 10d, the OCT light 13 is generated from the common light 37 to the Stokes light 11 but the fibers 21a and 23a are applied for generating the Stokes light 11 and OCT light 13 respectively to get optimum spectra for generating the CARS light 17 and OCT interference light 16 respectively.

FIG. 20 shows yet another embodiment of the system 1 including an optical system 10e. This optical system 10e includes a generating optical path 38 that is configured to generate the OCT light (third light) 13 from the leaser light 30a that is common with the Stokes light (first light) 11 and the pump light (second light) 12. In this optical system 10e, the quality of the generated OCT spectrum may be quite different for the above explained embodiments since the probe signal 14 is a picosecond pulse, the laser source 30a for the pump signal 12 is a femtosecond pulse.

FIG. 21 shows yet another embodiment of the system 1 including an optical system 10f. This optical system 10f includes a generating optical path 38 that is configured to generate the OCT light (third light) 13 from the common leaser light 30a by a switching element 38a that switches the laser light 30a to the OCT light path 23 and the light paths 21 and 22 for the Stokes light 11 and the pump light 12 in time-division manner.

In this specification, a system 1 for using the CARS light and the OCT light comprises: (a) a first unit 21 that is configured to emit a first light 11 with a first range of wavelengths: (b) a second unit 22 that is configured to emit a second light 12 with a second range of wavelengths shorter than the first range: (c) a third unit 23 that is configured to emit a third light 13 with a third range of wavelengths shorter than the second range: (d) an optical unit 25 that is configured to coaxially output the first light 11, the second light 12, and the third light 13 to a target (sample) 5 and acquire a light from the target 5: (e) a reference unit 34 that is configured to split off a reference light 13r from the third light 13: (f) a selecting unit 28b that is configured to select a reflected light 15 of the third light and a CARS light 17 with a range of wavelengths at least partially overlapping the third range from the acquired light and the CARS light is generated by the first light and the second light at the target; and (g) a detector 50 configured to detect the CARS light 17 and an interference light 16 that is combination of the reference light 13r and the reflected third light 15. The first light 11 may be a Stokes light (Stokes beam), the second light 12 may be a pump light (pump beam), and the third light 13 may be a light (beam) for OCT.

A method is also disclosed in this specification. The method comprise: (i) emitting a first light 11 with a first range of wavelengths and a second light 12 with a second range of wavelengths shorter than the first range via an optical unit 25 that is configured to coaxially output the first light 11 and the second light 12 to a target 5, and acquiring a light from the target 5: (ii) detecting a CARS light 17 by a detector through a selecting unit 28b that is configured to select the CARS light 17 generated by the first light 11 and the second light 12 from the acquired light: (iii) emitting a third light 13 with a third range of wavelengths shorter than the second range and at least partially overlapping a range of wavelengths of the CARS light 17 through the optical unit 25 to the target 5; and (iv) detecting an interference light 16 by the detector 50, wherein the interference light 16 is combination of (multiplexed with) a reference light 13r split off from the third light 13 and a reflected third light 16 acquired through the optical unit 25.

The system 1 further including a fourth unit 24 is also disclosed in this specification. The fourth unit 24 is configured to emit a fourth light (probe light, probe beam) 14 with a fourth range of wavelength shorter than the second range and larger than the third range to generate the CARS (TD-CARS, time-delay CARS, time resolved CARS) light 17 having a range of wavelengths at least partly overlapping the third range for the OCT light 13 and shorter than the fourth range. The fourth unit 24 may include a time delay unit 24a that is configured to control a time difference between the fourth light and the second light. Also, the method further including emitting the fourth light 14 is disclosed in the specification.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the appended claims.

The invention claimed is:

1. A system comprising:
   a Stokes light path configured to supply a Stokes light with a first range of wavelengths for emitting to a target via an optical I/O path;
   a pump light path configured to supply a pump light with a second range of wavelengths, wherein wavelengths in the second range of wavelengths have shorter wavelengths than wavelengths in the first range of wavelengths, for emitting to the target via the optical I/O path;
   a probe light path configured to supply a probe light with a range of probe light wavelengths, wherein the probe light wavelengths are shorter than wavelengths of a first CARS light which is generated by the Stokes light and the pump light only, for emitting to the target via the optical I/O path; and
   a detector configured to detect a second CARS light with a range of wavelengths, wherein wavelengths of the second CARS light are shorter than the wavelengths of the probe light, wherein the second CARS light is generated by the Stokes light, the pump light, and the probe light at the target.

2. The system according to claim 1, wherein the probe path is configured to emit the probe light at a time at least one of prior to, at the same time of, and delayed to the emitting the pump light and the Stokes light.

3. The system according to claim 1, wherein the probe path includes a time delay path configured to control a delay time of the probe light to the emitting the pump light, and
   the detector is configured to detect the second CARS light according to the probe light with the delayed time.

4. The system according to claim 1, further comprising an analyzer that is configured to analyze at least a part of compositions of the target using detection results of the second CARS light.

5. The system according to claim 3, further comprising an analyzer that is configured to analyze at least a part of compositions of the target using detection results of the second CARS generated by the probe light with the delayed time.

6. The system according to claim 1, wherein the Stokes light path is configured to emit the Stokes light with pulses having one to several hundred femtosecond pulse widths,
   the pump light path is configured to emit the pump light with pulses having one to several hundred femtosecond pulse widths, and
   the probe light path is configured to emit the probe light with pulses having one to several tens picosecond pulse widths.

7. A method comprising:
   emitting a Stokes light with a first range of wavelengths and a pump light with a second range of wavelengths, wherein wavelengths in the second range of wavelengths have shorter wavelengths than wavelengths in the first range of wavelengths, to a target;
   emitting a probe light with a range of probe light wavelengths, wherein the probe light wavelengths are shorter than wavelengths of a first CARS light which is generated by the Stokes light and the pump light only, to the target;
   detecting a second CARS light with a range of wavelengths, wherein wavelengths of the second CARS light are shorter than wavelengths of the probe light, wherein the second CARS light is generated by the Stokes light, the pump light, and the probe light at the target.

8. The method according to claim 7, wherein the emitting the probe light includes emitting the probe light at a time at least one of prior to, at the same time of, and delayed to the emitting the pump light and the Stokes light.

9. The method according to claim 7, wherein the emitting the probe light includes controlling a delay time of the probe light to the emitting the pump light and the Stokes light, and
   the detecting includes the second CARS light according to the probe light with the delayed time.

10. The method according to claim 7, further includes analyzing at least a part of compositions of the target using detection results of the second CARS light.

11. The method according to claim 9, further includes analyzing at least a part of compositions of the target using detection results of the second CARS light generated by the probe light with the delayed time.

12. A nontransitory computer readable medium encoded with a computer program product for a computer to operate a device including a path for emitting a light to a target via an optical I/O path and a detector for detecting a light from the target, wherein the computer program includes executable codes for performing steps of:
    emitting a Stokes light with a first range of wavelengths and a pump light with a second range of wavelengths, wherein wavelengths in the second range of wavelengths have shorter wavelengths than wavelengths in the first range of wavelengths shorter than the first range of wavelengths to the target via the optical I/O path;
    emitting a probe light with a range of wavelengths shorter than a range of wavelengths of a first CARS light which is generated by the Stokes light and the pump light only, to the target via the optical I/O path;
    detecting a second CARS light, by the detector, with a range of wavelengths shorter than the range of wavelengths of the probe light, generated by the Stokes light, the pump light, and the probe light at the target.

* * * * *